United States Patent [19]

Toda et al.

[11] Patent Number: 4,977,180

[45] Date of Patent: Dec. 11, 1990

[54] NOVEL PROLINAL DERIVATIVES

[75] Inventors: Masaaki Toda, Osaka; Shuichi Ohuchida, Kyoto; Hiroyuki Ohno, Shiga, all of Japan

[73] Assignee: Ono Pharmaceutical Co., Ltd., Osaka, Japan

[21] Appl. No.: 151,862

[22] Filed: Feb. 3, 1988

[30] Foreign Application Priority Data

Feb. 4, 1987 [JP] Japan ................... 62-22407

[51] Int. Cl.$^5$ ............... A61K 31/40; C07D 207/08
[52] U.S. Cl. ................... 514/423; 548/539; 548/540
[58] Field of Search ............. 548/539, 540; 514/423

[56] References Cited

U.S. PATENT DOCUMENTS 4,701,465 10/1987 Tanaka et al. ............... 548/540 X
4,743,616 5/1988 Tanka et al. ................ 548/540 X

FOREIGN PATENT DOCUMENTS 0154353 9/1985 European Pat. Off. .
0172458 2/1986 European Pat. Off. .
201741 11/1986 European Pat. Off. .
201742 11/1986 European Pat. Off. .
201743 11/1986 European Pat. Off. .
0268190 5/1988 European Pat. Off. ......... 548/540
0275482 7/1988 European Pat. Off. ......... 548/540
61-183297 8/1986 Japan .
3066162 3/1988 Japan ..................... 548/539

OTHER PUBLICATIONS

*Science,* 211, (1981), pp. 601–603; Weingartner, et al.
*J. Biochem.,* 94, (1983), pp. 1179–1189; Yoshimoto, et al.
*Protein, Nucleic Acid & Enzyme* 25(6), 513 (1980); Yoshimoto, et al.
*Nippon Nougei Kagaku Kaishi* 58(11), 1147 (1984); Yoshimoto, et al.
*J. Neurochem.,* 41, (1983), pp. 69–74; Wilk, et al.
*J. Neurochem.,* 42, (1984), pp. 237–241; Friedman, et al.

*Primary Examiner*—Joseph P. Brust
*Attorney, Agent, or Firm*—Sughrue, Mion, Zinn, Macpeak & Seas

[57] ABSTRACT

A novel prolinal derivative of general formula:

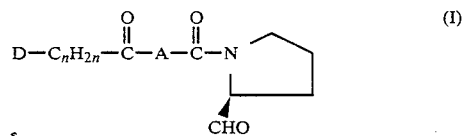

wherein A represents alkylene group of from 1 to 4 carbon atom(s) or saturated hydrocarbon ring of from 3 to 7 carbon atoms, n represents a number 2, 3 or 4, D represents carbocyclic or heterocyclic ring unsubstituted or substituted by from one to three of halogen atom, alkyl or alkoxy group of from 1 to 4 carbon atom(s), nitro group or trifluromethyl group posses inhibitory activity on prolyl endopeptidase, and therefore are useful for treating and/or preventing agent for amnesia.

13 Claims, No Drawings

NOVEL PROLINAL DERIVATIVES

SUMMARY

This invention is related to novel compounds having an inhibitory activity on prolyl endopeptidase.

More particularly, this invention is related to
(1) Novel prolinal derivatives having an inhibitory activity on prolyl endopeptidase, of the following general formula:

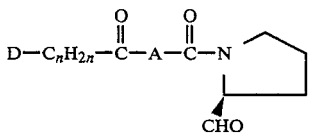

(I)

wherein all of the symbols are the same meaning as defined hereafter.

(2) processes for the preparation of them, and
(3) anti-amnesia agents containing them as active ingredient.

BACKGROUND

Recent advances in neuroscience are making clear the natural shape of neurotransmitters, substances deeply related to memory in brain. It is said that some of these substances are neuropeptides containing prolines.

Recovery of the memory was reported by the dosage of a neuropeptide containing proline to an experimental amnesia rat (See Science 211, 601 (1981)).

On the other hand, it is presumed that these neuropeptide - hormons shall be metabolized by cerebral endogenous peptidases. Especially, prolyl endopeptidase (EC, 3. 4. 21. 26) might intimately take part in such metabolism closely (See J. Biochem., 94, 1179 (1983)).

From these facts, studies were in progress based on the conclusion that it should be possible to prevent or treat amnesia by inhibiting prolyl endopeptidase and suppressing the metabolism of neutrotransmitter. (See Protein, Nucleic acid and Enzyme 25(6), 513(1980); Nippon Nougei Kagaku Kaishi 58(11), 1147(1984); J. Neurochem., 41, 69(1983); ibid 42, 237(1984).)

For the purpose described above, several compounds were synthesized. For example, it is clear that N-benzyloxycarbonyl-glycyl-L-prolyl-chloromethane, N-benzyloxycarbonyl-L-propyl-prolinal strongly inhibits prolyl endopeptidase (See J. Neurochem., 41, 69 (1983)). More recently, it is disclosed that the compounds shown below are effective for the above purpose.

(i) Prolinal derivatives of the general formula:

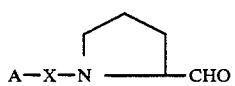

(A)

wherein A represents a protecting group of amino acid group in the field of amino acid chemical, and X represents a residual group of amino acid. See Japanese Patent Kokai No. 60-188317, i.e., European Patent Publication No. 154353.

(ii) N-acylpyrrolidine derivatives of the general formula:

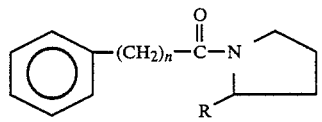

(B)

wherein n represents a number of 1~4, and R represents lower alkyl ester group, —CH$_2$OH group or aldehyde group.

See Japanese Patent Kokai No. 61-37764; a compound wherein n is 5 is also disclosed by correction, i.e., European Patent Publication No. 172458.

(iii) Compounds of the general formula:

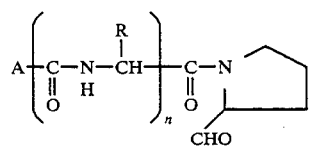

(C)

wherein A represents methyl group or benzyloxy group, R represents isopropyl group or isobutyl group on the condition that plural R's have the same meaning in one formula. And n represents 2 or 3.

See Japanese Patent Kokai No. 61-183297.

Most recently, five applications related to anti-amnesia agents having prolinal skeltons were published, i.e.:

(iv) Compounds of the general formula:

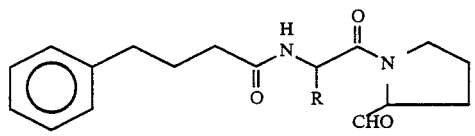

(D)

wherein R represents a group of

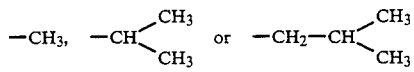

See Japanese Patent Kokai No. 61-238775, i.e., European Patent Publication No. 201741.

(v) N-acylpyrrolidine derivatives of the general formula:

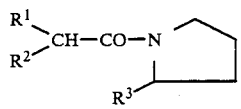

(E)

wherein $R^3$ represents lower alkyloxycarbonyl group, hydroxymethyl group or formyl group, $R^1$ represents a hydrogen atom or lower alkyl group, $R^2$ represents phenyl group or a group of the following general formula:

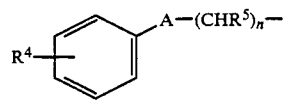

wherein R[4] represents a hydrogen atom, a halogen atom or lower alkoxy group, R[5] represents a hydrogen atom or lower alkyl group, n represents 1 or 1, A represents an oxygen atom, methylene group, hydroxymethylene group, phenylmethylene group or carbonyl group. or R[1] and R[2] represent, together with, benzylidene group unsubstituted or substituted by aromatic ring(s).

See Japanese Patent Kokai No. 61-238776, i.e., European Patent Publication No. 201742.

(vi) Compounds of the general formula:

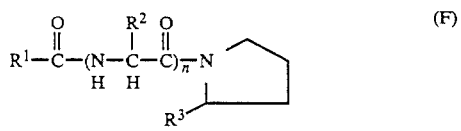

(F)

wherein n represents a number of 0~2, R[1] represents a straight-chained organic group of from 5 to 25 carbon atoms which is saturated or unsaturated, wherein an unsaturated carbon chain may contain a plural number of double bonds, R[2] represents a group of

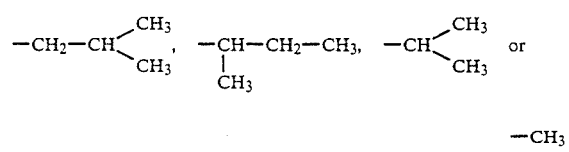

and R[3] represents lower alkyl ester group, —CH$_2$OH group or aldehyde group. See Japanese Patent Kokai No. 61-238799, i.e., European Patent Publication No. 201743.

(vii) Compounds of the general formula:

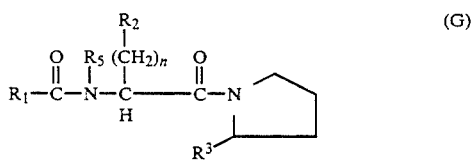

(G)

wherein n is an integer of more than one, R$_1$ is a saturated or unsaturated straight-chained hydrocarbon group of from 5 to 25 carbon atoms, wherein said unsaturated carbon chain may contain a plural number of double bonds, R[3] represents lower alkyl ester group of the formula: —COOR[4] (wherein R[4] represents lower alkyl group, hydroxymethyl group or formyl group, R[2] represents methyl group, phenyl group, hydroxyphenyl group, indolyl group, imidazolyl group, carboxyl group, formyl group, amino group, hydroxy group, hydroxyalkyl group, thiol group, methylothio group or guanidino group etc., and each of above groups may be substituted and R[5] represents a hydrogen atom or a single bond between a carbon atom and nitrogen atom together with R[2] when n is 3.

See Japanese Patent Kokai No. 62-84058, i.e. European Patent Publication No. 201743.

(viii) Dipeptide derivatives of the general formula:

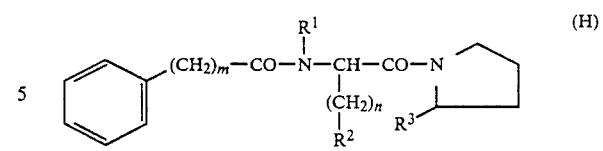

(H)

wherein m represents an integer of 1~8, n represents an integer of 1~6, R[1] represents a hydrogen atom, R[2] represents a hydrogen atom, a branched alkyl group of from 3 to 5 carbon atoms, phenyl group, hydroxyphenyl group, indolyl group, imidazolyl group or methylthio group, or a single bond between a carbon atom and a nitrogen atom together with R[1] and R[3] represents lower alkyl ester group, hydroxymethy group or formyl group.

See Japanese Patent Kokai No. 62-148467, i.e., European Patent Publication No. 201741.

The present inventors have also filed an application related to prolinal derivatives having an anti amnesia activity, in advance of the present application, i.e.

(ix) Prolinal derivatives of the general formula:

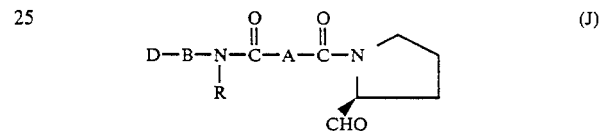

(J)

wherein A represents alkylene or alkenylene group of from 1 to 8 carbon atom(s) or a saturated hydrocarbon ring of from 3 to 7 carbon atoms, R represents a hydrogen atom, phenyl group, benzyl group, alkyl group of from 1 to 8 carbon atoms(s) or cycloalkyl group of from 3 to 7 carbon atoms, B represents alkylene group of from 1 to 8 atoms(s) unsubstituted or substituted by phenyl group or benzyl group, or a single bond, D represents carbocyclic or heterocyclic ring unsubstituted or substituted by from one to three of halogen atom, alkyl or alkoxy group of from 1 to 4 carbon atom(s), nitro group or trifluoromethyl group.

See Japanese patent Kokai No. 62-290631, i.e., European Patent Application No. 87116613.8.

COMPARISON WITH THE PRIOR ART

The compounds of the present invention of the general formula (I) have a prolinal (pyrrolidine-2-al) skeleton in their structure and have an inhibitory activity on prolyl endopeptidase, being somewhat the same as the compounds of the general formula (A)~(J) and the compounds in the literature [J. Neurochem., 41, 69 (1983].

But the compounds of the present invention are novel compounds which have a different structure from the compounds with the general formula (A)~(J).

That is, the modification that the oxo group is introduced in the alkylene chain between a benzene ring and a prolinal has been known (described in (v) prior art: see Japanese Patent Kokai No. 61-238776, i.e., European Patent Publication No. 201743, and, in the specification, the oxo group combines directly to a benzene ring.

The compounds of the present invention also have introduced a longer alkylene chain between the benzene ring and the oxo group of general formula (E), described in Prior Art, and we found that these compounds have an inhibitory activity on prolyl endopeptidase.

Further, in certain compounds, we tried the modification described hereinafter: to change part of A of the general formula (I) to a saturated hydrocarbon ring, to introduce substituent groups into 1 benzene ring or to replace a benzene ring by a naphthalene ring.

Then we found all these modified compounds have an inhibitory activity on prolyl endopeptidase.

And we, the present inventors, confirmed in the previous application (compounds represented by the general formula (J)) that compounds wherein a benzene ring was replaced by other aromatic rings (including heterocyclic rings and saturated rings, e.g., naphthalene, fluorene, furan rings) also maintained the inhibitory activity on prolyl endopeptidase with several modification in D.

Among the compounds of the present invention which are modified compounds of the general formula (J) in the parts other than D, it is not difficult to forecast that the compounds wherein D was replaced by the other rings should have maintained the activity, if the compounds wherein D is benzene ring have enough activity.

DISCLOSURE OF THE INVENTION

The present invention is related to (1) A novel prolinal derivative of the general formula:

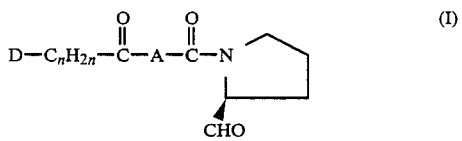

wherein A represents alkylene group of from 1 to 4 carbon atom(s) or saturated hydrocarbon ring of from 3 to 7 carbon atoms, n represents a number of 2, 3 or 4, D represents carbocyclic or heterocyclic ring unsubstituted or substituted by from one to three of halogen atom, alkyl or alkoxy group of from 1 to 4 carbon atom(s), nitro group or trifluoromethyl group.

(2) Processes for the preparation of them; and (3) Anti-amnesia agents containing them as an active ingredient.

In the general formula (I), "alkylene group of from 1 to 4 carbon atom(s)" represented by A means methylene, ethylene, trimethylene and tetramethylene groups and isomeric groups thereof.

In the general formula (I), "saturated hydrocarbon ring of from 3 to 7 carbon atoms" represented by A means cyclopropane, cyclobutane, cyclopentane, cyclohexane and cycloheptane rings.

In the general formula (I), halogen atoms in D means fluorine, chlorine, bromine, iodine atoms, and alkyl group of from 1 to 4 carbon atom(s) means methyl, ethyl, propyl and butyl groups and isomeric groups thereof, and alkoxy group of from 1 to 4 carbon atom(s) means methoxy, ethoxy, propoxy and butoxy groups and isomeric groups thereof.

In the general formula (I), "carbocyclic ring" represented by D means mono-, bi- or tri-cyclic aromatic carbocyclic ring(s) containing not more than 15 carbon atoms which may be partially or fully saturated.

Examples of the rings mentioned above are benzene, naphthalene, indene, azulene, fluorene, phenanthrene, anthracene, acenaphthalene, biphenylene rings and partially or fully saturated rings thereof.

In the general formula (I), "heterocyclic ring" represented by D means mono-, bi- or tri-aromatic heterocyclic ring(s) containing not more than 15 carbon and hetero atoms which may be partially or fully saturated. In the above heterocyclic rings, rings containing one or two hetero atom(s) are preferred.

Examples of the rings mentioned above are furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, chromene, quinoline, isoquinoline, quinolizine, purine, indazole, quinazoline, cinnoline, quinoxaline, phthalazine, pteridine, carbazole, acridine, phenanthridine, xanthene, phenazine, phenothiazine rings and partially or fully saturated rings thereof.

In the general formula (I), preferred rings represented by D especially are benzene and naphthalene rings and partially saturated rings thereof.

In the above rings, substituted benzene rings are preferred as substituted rings with substituent(s).

Throughout the specification including the claims, stereo isomers generated by stereo configuration(s) (asymmetric carbon, etc.) and structural isomers generated by branding of carbon chain, etc. are included in the present invention.

For example, it may be easily understood that alkylene and alkenylene groups include straight-chained and also branched-chained ones, to the skilled in the art.

Rings represented by A or rings in D may be attached to the adjoined group at any position.

The compounds of the present invention of the general formula (I) can be separated into two groups of compounds represented by the general formula:

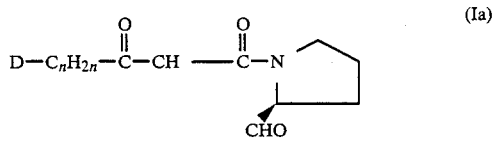

and

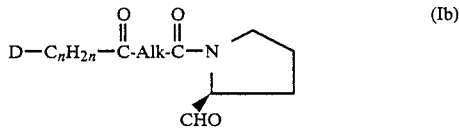

wherein

—CH represents saturated hydrocarbon ring of from 3 to 7 carbon atoms, Alk represented alkylene group of from 1 to 4 carbon atoms and the other symbols are the same meaning as defined hereinbefore.

PROCESS FOR THE PREPARATION

According to the present invention, the compounds of the present invention of the general formula (I) may be prepared by oxidizing prolinol derivatives of the general formula:

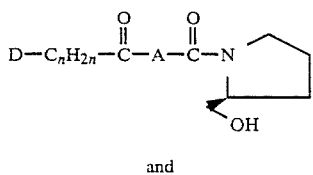

(II)

and

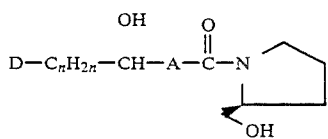

(III)

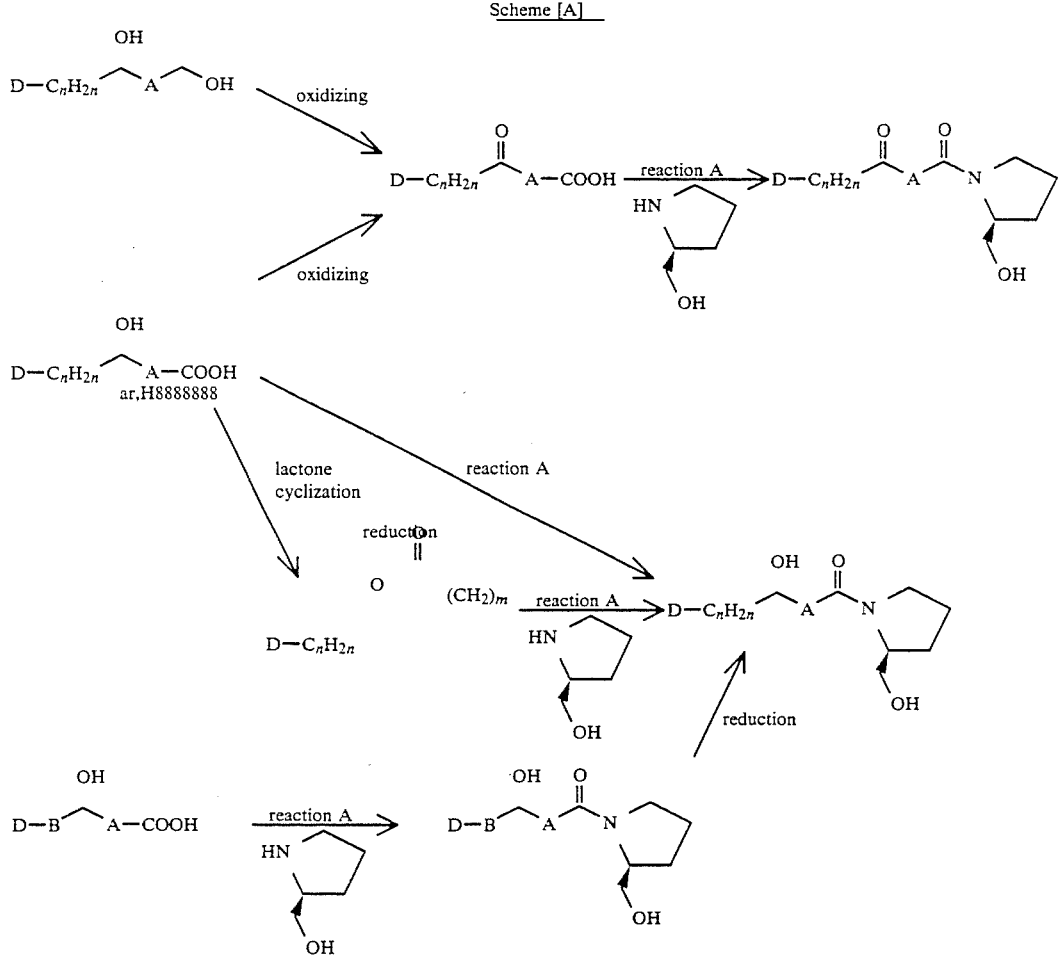

wherein all of the symbols are the same meaning as defined hereinbefore under mild conditions.

Oxidation under mild conditions is known and may be carried out, for example, using an oxidation agent (sulfur trioxide - pyridine complex, chromium trioxide - pyridine complex, t-butyl chloroformate, oxalyl chloride etc.), with or without a tertiary amine (triethylamine, pyridine etc.), in an inert organic solvent (DMSO, methylene chloride, chloroform, benzene etc.), at a temperature of from 0° C. to 50° C.

PROCESS FOR THE INTERMEDIATES

Prolinol derivatives represented by the general formula (II) or (III) may be prepared according to a series of reactions in scheme [A] shown hereinafter.

In the scheme [A], each symbol has the same means as defined hereinafter, or has the same meaning as defined hereinbefore.

B—alkenyl or alkynyl group of from 2 to 4 carbon atoms.

m—1, 2, 3 or 4.

Reaction A is the reaction of forming an amide-bond.

All reactions, described in the scheme [A], may be carried out by a known method, and the starting materials and reagents used in each reaction are all known per se or may be prepared by a known method.

Throughout the specification, in each reaction, products may be purified by conventional methods, for example, distillation at atmospheric or reduced pressure, high performance liquid chromatography, thin layer chromatography using silica gel or magnesium silicate or washing or recrystallization. Purification may be carried out after each reactions or a series of reactions.

PHARMACOLOGICAL ACTIVITIES

The compounds of the present invention of the general formula (I) possess an inhibitory activity on prolyl endopeptidase as described before. For example, in a standard laboratory test, results in the followings are given.

Prolyl endopeptidase inhibitory activity in vitro

The compounds of the present invention showed activities as in the following Table I, with the test system described hereafter.

TABLE I

| Example No. of the compounds | Concentration for 50% inhibition IC$_{50}$ (mN) |
|---|---|
| 1 | 27 |
| 1 (a) | 120 |
| 1 (d) | 150 |
| 1 (e) | 50 |
| 1 (f) | 62 |
| 1 (g) | 84 |
| 1 (h) | 29 |
| 1 (i) | 11 |
| 1 (j) | 32 |
| 1 (k) | 18 |
| 1 (l) | 39 |
| 1 (m) | 15 |
| 1 (b) | 14 |
| 1 (c) | 24 |

Inhibitory activity of prolyl endopeptidase in vitro was measured by the following test system.

A mixed solution of 20 mM tris-HCl buffer (pH 7.5; 935 μl; containing 10 mM EDTA and 10 mM mercaptoethanol), a solution of a compound of the present invention in DMSO (10 μl) and a solution of prolyl endopeptidase which was purified from bovine brain (0.13 unit; prepared by the method described in J. Biochem., 94, 1179 (1983)) in tris-HCl buffer (15 μl) was preincubated for 15 mins at 37° C.

To the solution, 5 mM of N-benzyloxycarbonyl-glycyl-prolyl-p-nitroanilide (40 μl) in a mixture of 40% dioxane-60% water was added. The solution was incubated for 1 min at the same temperature.

Optical absorption ($a_1$) at 405 nm of the solution, and optical absorption ($a_2$) at 405 nm of the solution after 30 mins' further incubation at 37° C. were measured.

Optical absorptions ($b_1$ and $b_2$) of the solutions using DMSO instead of the solution of the compound of the present invention were also measured.

Inhibitory ratio was calculated by the following expression and IC$_{50}$ (required concentration for 50% inhibition) was obtained (See Protein, Nucleic acid and Enzyme 25(6), 513, 1980.).

$$\text{Inhibitory ratio (\%)} = \frac{(b_2 - b_1) - (a_2 - a_1)}{b_2 - b_1} \times 100$$

TOXICITY

On the other hand, it was confirmed that the toxicity of the compounds of the present invention was very low. Therefore, the compounds of the present invention may be considered to be sufficiently safe and suitable for pharmaceutical use.

APPLICATION FOR PHARMACEUTICALS

To inhibit prolyl endopeptidase is to suppress the metabolism of neurotransmitters, substances taking part in memory in the brain (each of them is a peptide) as described hereinbefore, and therefore such can be useful for prevention and/or treatment of amnesia, in animals including human beings, especially human beings.

The compounds of the present invention possess an inhibitory activity on prolyl endopeptidase in vitro, so they are expected to be useful for prevention and/or treatment of amnesia.

For the purpose above described, the compounds of the present invention may normally by administered systemically or partially, usually by oral or parenteral administration.

The doses to be administered are determined depending upon age, body weight, symptom, the desired therapeutic effect, the route of administration, and the duration of the treatment, etc. In the human adult, the doses per person per dose are generally between 1 mg and 500 mg, by oral administration, up to several times per day, and between 1 mg and 100 mg, by parenteral administration (preferably, intravenous administration) up to several times per day.

As mentioned above, the doses to be used depend upon various conditions. Therefore, there are cases in which doses lower than or greater than the ranges specified above may be used.

At the administration, the compounds of the present invention may be formed into solid compositions, liquid compositions or other compositions for oral administration, injection compositions, external composition, suppositories, etc., for parenteral administration.

Solid compositions for oral administration, include compressed tablets, pills, dispersible powders, capsules, and granules. In such compositions, one or more of the active compound(s) is or are admixed with at least one inert diluent (lactose, mannitol, glucose, hydroxypropylcellulose, microcrystalline cellulose, starch, polyvinylpyrrolidone, magnesium metasilicate aluminate etc.). The compositions may also comprise, as is normal practice, additional substances other than inert diluents: e.g. lubricating agents (magnesium stearate, etc.), disintegrating agents (cellulose calcium gluconate, etc.), assisting agents for dissolving (glutamic acid, aspertic acid, etc.) and stabilizing agents (lactose, etc.).

The tablets or pills may, if desired, be coated with a film of gastric or enteric material (sugar, gelatin, hydroxypropylcellulose or hydroxypropylmethyl cellulose phthalate, etc.).

Capsules include soft ones and hard ones.

Liquid compositions for oral administration include pharmaceutically-acceptable solutions, emulsions, suspensions, syrups and elixirs.

In such compositions, one or more of the active compound(s) is or are used in inert diluent(s) commonly used in the art (purified water, ethanol, etc.).

Besides inert diluents, such compositions may also comprise adjuvants (wetting agents, suspending agents, etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g., stabilizing agents (sodium sulfite, etc.) isotonic buffer (sodium chloride, sodium citrate, citric acid, etc.).

For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such compositions, one or more active compound(s) is or are admixed with at least one inert aqueous diluent(s) (distilled water for injection, physiological salt solution, etc.) or inert non-aqueous diluent(s) (propylene glycol, polyethylene glycol, olive oil, ethanol, POLYSOLBATE 80 (registered trade mark), etc.).

Injections may comprise other than inert diluents: e.g., preserving agents, wetting agents, emulsifying agents, dispersing agents, stabilizing agents (lactose, etc.) and assisting agents such as assisting agents for dissolving (glutamic acid, aspertic acid, etc.).

They may be sterilized, for example, by filtration through a bacteria-retaining filter, by incorporation of sterilizing agents in the compositions or by ;irradiation. They also be manufactured in the form of sterile solid compositions, for example, by freeze-drying, and which can be dissolved in sterile water or some other sterile diluents for injection immediately before used.

Other compositions for parenteral administration include liquids for external use, and endermic liniments (ointment, etc.), suppositories and pessaries which comprise one or more of the active compound(s) and may be prepared by known methods.

REFERENCE EXAMPLES AND EXAMPLES

The following reference examples and examples illustrate the present invention, but do not limit the present invention.

The solvents in the parentheses show the developing or eluting solvents and the ratios of the solvents used are by volume in chromatographic separations.

Unless otherwise specified, "IR" were measured by a liquid film method, and "NMR" were measured using CDCl₃.

REFERENCE EXAMPLE 1

Synthesis of 7-phenyl-4-oxoheptanoic acid

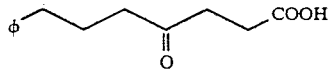

Jones' reagents (3.4 ml; 2.6N) was added to acetone solution (6 ml) of 7-phenylheptane-1,4-diol (630 mg), stirred for 1 hr.

The reaction mixture was diluted with ethylether, washed with water and saturated aqueous solution of sodium chloride, successively, dried and evaporated to give the title compound (580 mg, partly, containing corresponded lactone) having the following physical data:

TLC: Rf 0.14 and 0.43 (hexane:EtOAc=1:1)

REFERENCE EXAMPLE 2

Synthesis of N-(7-phenyl-4-oxoheptanoyl)-L-prolinal

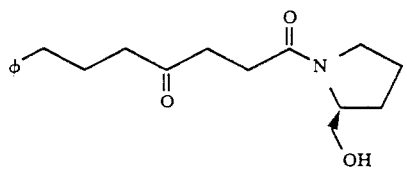

In an atmosphere of argon, diisopropylcarbodiimide (0.5 ml) was added to the solution of methylene chloride (6 ml) of carbonic acid prepared in reference example 1 and the solution was stirred for 30 minutes.

L-prolinal (0.31 ml) was added thereto, and the reaction mixture was stirred for 1 hr and left as it was for 18 hr at −5° C.

The reaction mixture was evaporated, and the residue was purified by column chromatography on silica gel (hexane - EtOAc) to give the title compound (219 mg) having the following physical data:

TLC: Rf 0.20 (EtOAc);
NMR: δ 71–7.35 (5H,m), 4.05–4.25 (1H,m), 3.40–3.75 (4H,m), 2.40–2.80 (8H,m), 1.8–2.2 (6H,m).

REFERENCE EXAMPLE 3

Synthesis of 2-[3-(2-nitrophenyl)propyl]tetrahydrofuran-5-one

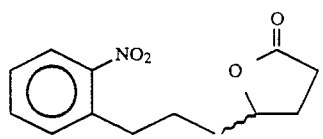

2-(3-phenylpropyl)tetrahydrofuran-5-one (230 mg) was dissolved in anhydrous acetic acid (1 ml), cooled with ice.

Concentrated nitric acid was added dropwise to the mixture.

20 mins later, the reaction mixture was stirred for 30 mins at room temperature.

Ethyl acetate was added to the reaction mixture and an oily layer was washed with successive saturated aqueous solution of sodium bicarbonate and saturated aqueous solution of sodium chloride, and dried.

The residue was purified by column chromatography on silica gel (EtOAc:hexane=1:1) to give the title compound (255 mg) having the following physical data:
TLC: Rf 0.21 or 0.24 (EtOAc:hexane=1:1).

REFERENCE EXAMPLE 4

Synthesis of N-[4-hydroxy-7-(2-nitrophenyl)heptanoyl]-L-prolinal

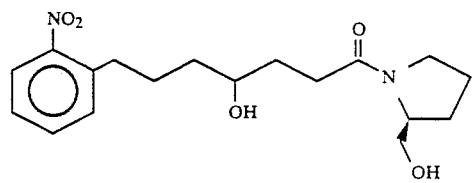

L-prolinal (163 μl) was added to the solution of THF (5 ml) of lactone (prepared in reference example 3) and cooled with ice.

Sodium hydride was added to the reaction solution and the same stirred for 30 mins at the same temperature.

The reaction solution was controlled to acidic with 1N hydro chloride, and ethyl acetate was added to the solution.

The oily layer was dried and evaporated to give the title compound having the following physical data:
TLC: Rf 0.14 (EtOAc:CH₃OH=95:5).

EXAMPLE 1

Synthesis of N-(7-phenyl-4-oxoheptanoyl)-L-prolinal

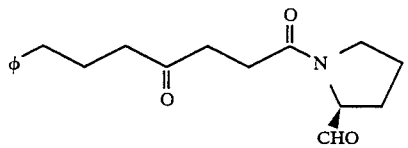

Triethylamine (0.32 ml) was added to the solution of dried-DMSO (1 ml) of prolinol (105 mg; prepared in reference example 2).

A solution of DMSO (1 ml) of sulfur trioxide-pyridine complex (185 mg) was added to the reaction solution and the same stirred for 20 mins at room temperature.

The reaction solution was poured into ice water.

The mixture was stirred, and then ethyl acetate was added to the mixture.

The oily layer was washed with successive, 1N hydrochloride and saturated aqueous solution of sodium chloride and dried.

Then the reaction mixture was evaporated.

The residue was purified by column chromatography on silica gel (EtOAc:hexane=8:2) to give the title compound (69.4 mg) having the follow physical data:

TLC: Rf 0.31 (EtOAc:Hexane—8:2);

IR: $\nu$ 2900, 1705, 1700, 1630, 1420, 735, 680 cm$^{-1}$.

EXAMPLE 1(a)~1(m)

By the same procedure as described in reference example 1, 2 and example 1, the compounds having the data described in the following Table II were prepared.

The compound of example 1(j) was prepared by using the compound of reference example 4 as starting material.

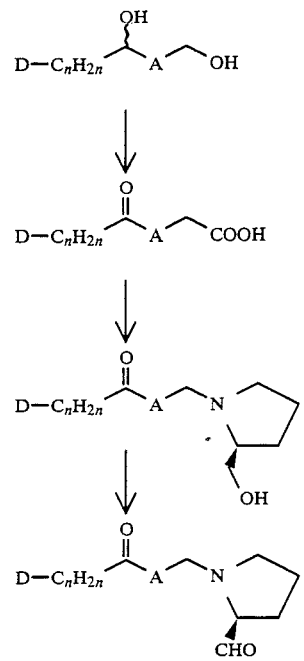

TABLE II

| Example No. | D—C$_n$H$_{2n}$—C(O)—A— | Name | TLC | IR (cm$^{-1}$) |
|---|---|---|---|---|
| 1 (a) | phenyl-(CH$_2$)$_2$-C(O)-(CH$_2$)$_2$- | N-(6-phenyl-4-oxohexanoyl) L-prolinal | Rf 0.40 (EtOAc) | $\nu$ 1725, 1710, 1625, 1435, 1395 |
| 1 (b) | phenyl-(CH$_2$)$_2$-C(O)-trans-cyclopentyl- | N-[trans-2-(3-phenylpropanoyl) cyclopentanecarbonyl]-L-prolinal | Rf 0.27 (hexane:EtOAc = 1:1) | $\nu$ 1715, 1690, 1620, 1410, 730, 690 |
| 1 (c) | phenyl-(CH$_2$)$_2$-C(O)-trans-cyclohexyl- | N-[trans-2-(3-phenylpropanoyl) cyclohexanecarbonyl]-L-prolinal | Rf 0.52 (hexane:EtOAc = 1:2) | $\nu$ 1715, 1690, 1610, 1410, 730, 685 |
| 1 (d) | phenyl-(CH$_2$)$_3$-C(O)-CH(iPr)- | N-(2RS-isopropyl-3-oxo-7-phenyl heptanoyl)-L-prolinal | Rf 0.43 (hexane:EtOAc = 1:1) | $\nu$ 2950~2850, 1715, 1620, 1400, 730, 690 |

TABLE II-continued

| Example No. | D—C$_n$H$_{2n}$—$\overset{\overset{\displaystyle O}{\|}}{C}$—A— | Name | TLC | IR (cm$^{-1}$) |
|---|---|---|---|---|
| 1 (e) | 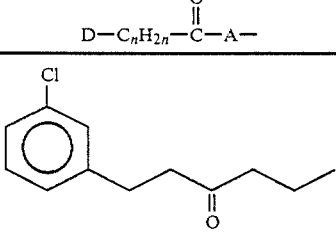 | N-[6-(3-chlorophenyl)-4-oxohexanoyl]-L-prolinal | Rf 0.67 (EtOAc) | ν 2920, 1720, 1705, 1630, 1430 |
| 1 (f) | 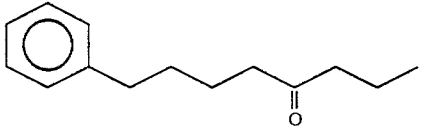 | N-(4-oxo-8-phenyloctanoyl)-L-prolinal | Rf 0.27 (hexane:EtOAc = 2:8) | ν 2800, 1710, 1630, 1420, 1360, 740, 690 |
| 1 (g) | 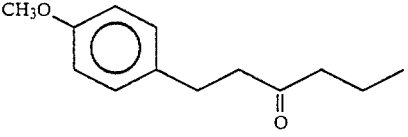 | N-[6-(4-methoxyphenyl)-4-oxohexanoyl]-L-prolinal | Rf 0.25 (hexane:EtOAc = 2:8) | ν 3400, 1710, 1620, 1500, 1420, 1235, 1170, 1020 |
| 1 (h) | 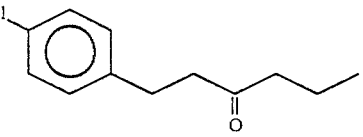 | N-[6-(4-chlorophenyl)-4-oxohexanoyl]-L-prolinal | Rf 0.30 (EtOAc) | ν 2900, 1710, 1620, 1480, 1420, 1080, 1000, 800 |
| 1 (i) | 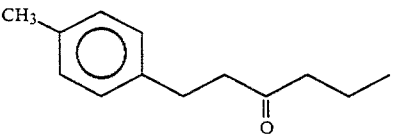 | N-[6-(4-methylphenyl)-4-oxohexanoyl]-L-prolinal | Rf 0.32 (hexane:EtOAc = 2:8) | ν 1700, 1620, 1420, 795 |
| 1 (j) | 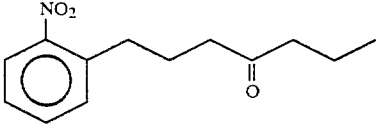 | N-[7-(2-nitrophenyl)-4-oxoheptanoyl]-L-prolinal | Rf 0.15 (EtOAc:MeOH 97:3) | ν 1720, 1705, 1630, 1510, 1430, 1420 |
| 1 (k) | 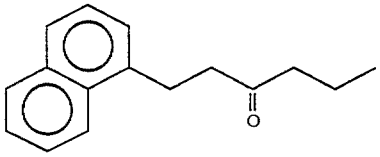 | N-[6-(1-naphthyl)-4-oxohexanoyl]-L-prolinal | Rf 0.31 (EtOAc) | ν 2830, 1710, 1630, 1425, 790, 770 745 |
| 1 (l) | 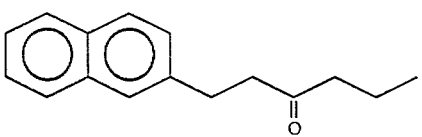 | N-[6-(2-naphthyl)-4-oxohexanoyl]-L-prolinal | Rf 0.31 (AcOEt) | ν 1710, 1630, 1420, 810, 740 |
| 1 (m) | 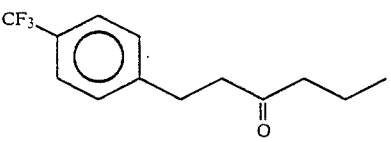 | N-[4-oxo-6-(p-trifluoromethylphenyl)hexanoyl]-L-prolinal | Rf 0.33 (hexane:AcOEt = 1:4) | ν 1710, 1630~1610, 1430, 1320, 1150,mx,1 1110, 1060, 1010, 820 |

FORMULATION EXAMPLE

The following components were admixed by a conventional method and punched out to obtain 100 tablets each containing 50 mg of active ingredient.

| | |
|---|---|
| N-(7-phenyl-4-oxoheptanoyl)-L-prolinal | 5 g |
| Cellulose calcium gluconate (disintegrating agent) | 0.2 g |
| Magnesium stearate (lubricating agent) | 0.1 g |
| Microcrystaline cellulose | 4.7 g |

What is claimed is:

1. A novel prolinal derivative of general formula:

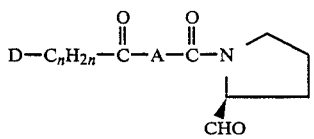  (I)

where A represents alkylene group of from 1 to 4 carbon atom(s) or saturated hydrocarbon ring of from 3 to 7 carbon atoms, n represents a number 2, 3 or 4, D represents mono-, bi- or tri-carbocyclic ring(s) containing not more than 15 carbon atoms which may be partially or fully saturated or aromatic, wherein the said ring(s) represented by D is unsubstituted or substituted by from one to three of halogen atom, alkyl or alkoxy group of from 1 to 4 carbon atom(s), nitro group or trifluoromethyl group.

2. A compound according to claim 1, D represents phenyl or naphthyl unsubstituted or substituted by from one to three of halogen atom, alkyl or alkoxy group of from 1 to 4 carbon atom(s) or nitro group.

3. A compound according to claim 1, which is a compound of the general formula:

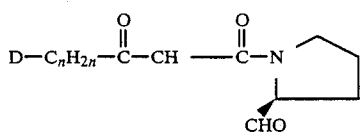  (Ia)

wherein

—CH represents saturated hydrocarbon ring of from 3 to 7 carbon atoms and the other symbols have the same meaning as defined in claim 1.

4. A compound according to claim 1 or 3, which is:
N-(trans-2-(3-phenylpropanoyl)cyclopentanecabonyl)-L-prolinal or
N-(trans-2-(3-phenylpropanoyl)cyclohexanecabonyl)-L-prolinal.

5. A compound according to claim 1, which is a compound of the general formula:

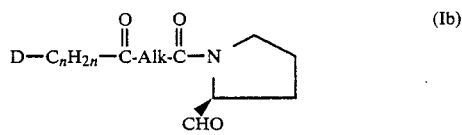  (Ib)

(wherein AlK represents alkylene group of from 1 to 4 carbon atom(s), the other symbols are the same meaning as defined in claim 1).

6. A compound according to claim 5 wherein D is unsubstituted naphthyl group.

7. A compound according to claim 1 or 6, which is:
N-(6-(1-naphthyl)-4-oxohexanoyl)-L-prolinal or
N-(6-(2-naphthyl)-4-oxohexanoyl)-L-prolinal.

8. A compound according to claim 5 wherein D is unsubstituted phenyl group.

9. A compound according to claim 1 or 8, which is:
N-(6-phenyl-4-oxohexanoyl)-L-prolinal,
N-(7-phenyl-4-oxoheptanoyl)-L-prolinal,
N-(8-phenyl-4-oxooctanoyl)-L-prolinal or
N-(2RS-isopropyl-3-oxo-7-phenylheptancy)-L-prolinal.

10. A compound according to claim 5 wherein D is unsubstituted phenyl group.

11. A pharmaceutical composition for treating amnesia which comprises, as an active ingredient, an effective amount of prolinal derivative of the general formula (I) depicted in claim 1 and pharmaceutical acceptable carrier and/or coating.

12. The method for treating amnesia which comprises administering a therapeutically effective amount of prolinal derivative of the general formula (I) depicted in claim 1.

13. A compound according to claim 1 or 10, which is:
N-(6-(4-methylphenyl)-4-oxohexanoyl)-L-prolinal,
N-(6-(4-methoxyphenyl)-4-oxohexanoyl)-L-prolinal,
N-(6-(4-chlorophenyl)-4-oxohexanoyl)-L-prolinal,
N-(6-(3-chlorophenyl)-4-oxohexanoyl)-L-prolinal,
N-(7-(2-nitrophenyl)-4-oxoheptanoyl)-L-prolinal or
N-(4-oxo-6-(p-trifluoromethylphenyl)hexanoyl)-L-prolinal.
N-(7-(2-nitrophenyl)-4-oxoheptanoyl)-L-prolinal or
N-(4-oxo-6-(p-trifluoromethylphenyl)hexanoyl)-L-prolinal.

* * * * *